US00PP24793P2

(12) United States Plant Patent

Deng et al.

(10) Patent No.: US PP24,793 P2

(45) Date of Patent: Aug. 19, 2014

(54) *GERBERA* PLANT NAMED 'UFGE 7031'

(50) Latin Name: *Gerbera hybrida*
Varietal Denomination: UFGE 7031

(71) Applicants: Zhanao Deng, Riverview, FL (US); Brent K. Harbaugh, Bradenton, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 13/986,122

(22) Filed: Apr. 3, 2013

(51) Int. Cl.
*A01H 5/00* (2006.01)

(52) U.S. Cl.
USPC ..... Plt./357

(58) Field of Classification Search
USPC ..... Plt./357
See application file for complete search history.

(56) References Cited

PUBLICATIONS

M.K, Hausbeck, W.R. Quackenbush, and S.D. Linderman, Michigan State University, Department of Plant Pathology, East Lansing, MI 48824. Evaluation of cultivars of African daisy for resistance to powdery mildew, 2002.

*Primary Examiner* — June Hwu
*Assistant Examiner* — Keith Robinson
(74) *Attorney, Agent, or Firm* — Christopher & Weisberg, P.A.

(57) ABSTRACT

A new and distinct *Gerbera* plant particularly distinguished by having a novel combination of traits including free flowering habit, medium lengths of peduncles, single orange-red inflorescence, orange-red discs before opening of disc florets, an overall inflorescence diameter of approximately 12 cm, high levels of resistance to powdery mildew, good heat tolerance, and potential to produce attractive plants in large (20 cm or larger diameter) containers, is disclosed.

3 Drawing Sheets

Genus and species: *Gerbera hybrida.*
Cultivar denomination: 'UFGE 7031'.

CROSS-REFERENCE TO RELATED APPLICATION n/a

ACKNOWLEDGEMENT OF FEDERAL RESEARCH REPORT n/a

BACKGROUND OF THE NEW CULTIVAR

The present invention relates to a new and distinct cultivar of *Gerbera hybrida* ("*Gerbera*") cultivar named 'UFGE 7031'.

*Gerbera* plants are ornamental plants from the family Asteraceae frequently used as a decorative garden plant or for cut flowers. The inflorescence of the *Gerbera* plant is a large capitulum with a plurality of florets, which are often brightly colored. The florets may include outer ray florets, trans florets, and central disk florets.

The new *Gerbera* cultivar 'UFGE 7031' is a product of a planned breeding program conducted by the Inventors in Wimauma, Fla. The objective of the breeding program is to develop new *Gerbera* cultivars with good plant vigor, moderate lengths of peduncles, numerous inflorescences, attractive inflorescence colors, large inflorescence sizes, and moderate to high levels of powdery mildew resistance.

The new *Gerbera* cultivar 'UFGE 7031' originated from a cross made in Wimauma, Fla., in 2005 between the female or seed parent 'UFGE 5004' (unpatented) and the male or pollen parent 'UFGE 5015' (unpatented). 'UFGE 5004' was a *Gerbera* breeding line that was selected by the inventors in Wimauma, Fla., from progeny of a cross made in Bradenton, Fla., in 2004 between the *Gerbera* breeding lines 'UFGE 31-19' (unpatented) and 'UFGE 5-23' (unpatented). The male parent 'UFGE 5015' was progeny of a cross between the commercial cultivar 'Sunburst Fuchsia' (unpatented) and a *Gerbera* breeding line 'UFGE 3714' (unpatented). The new *Gerbera* cultivar 'UFGE 7031' was selected by the inventors from the progeny of the stated parentage in summer 2007 in Wimauma, Fla.

The first asexual reproduction of the new *Gerbera* cultivar 'UFGE 7031' was accomplished by crown division in late 2007 in Wimauma, Fla. Since then, the new *Gerbera* has been asexually propagated by crown division and/or tissue culture for more than four generations. Asexually propagated plants of the new *Gerbera* have remained true to the original plant, and all characteristics of the new *Gerbera* have been transmitted and retained through three successive asexual vegetative generations.

Plant Breeder's Rights for this cultivar have not been applied for. The new *Gerbera* cultivar has not been made publicly available more than one year prior to the filing of this application.

SUMMARY OF THE INVENTION

Plants of the new *Gerbera* cultivar 'UFGE 7031' have not been observed under all possible environmental conditions. Its phenotype may vary significantly with variations in environment such as light intensity, temperature, and day length, and cultural practices such as fertilization and irrigation, without any variance in genotype.

The following traits are the most outstanding and distinguishing characteristics of this new and unique *Gerbera* cultivar when grown in Wimauma, Fla., under normal horticultural practices in greenhouse conditions which closely approximate those generally used in commercial practice:

1. Freely flowering habit;
2. Medium peduncle length of approximately 40 cm;
3. Single inflorescence type;
4. Orange-red (RHS 30C) ray florets;
5. Greyed-purple (RHS 187A) discs before opening of disc florets;
6. Inflorescence diameter of approximately 12 cm;
7. High level of resistance to powdery mildew; and
8. Good heat tolerance.

Plants of the new *Gerbera* cultivar 'UFGE 7031' differ from the female parent 'UFGE 5004' (unpatented) in the following characteristics:

1. Plants of the new *Gerbera* cultivar 'UFGE 7031' and the female parent 'UFGE 5004' differ in ray floret color as plants of the female parent have light pink ray florets; and
2. Plants of the new *Gerbera* 'UFGE 7031' and the female 'UFGE 5004' parent differ in disc floret color as plants of the female parent have yellow-green disc florets.

Plants of the new *Gerbera* cultivar 'UFGE 7031' differs from the male parent 'UFGE 5015' (unpatented) in the following characteristics:

1. Plants of the new *Gerbera* cultivar 'UFGE 7031' and the male parent 'UFGE 5015' differ in inflorescence form as plants of the male parent have semi-double inflorescences;
2. Plants of the new *Gerbera* cultivar 'UFGE 7031' and the male parent 'UFGE 5015' differ in ray floret color as the plants of the male parent have dark rose ray florets;
3. Plants of the new *Gerbera* cultivar 'UFGE 7031' and the male parent 'UFGE 5015' differ in disc floret color as the plants of the male parent have dark rose disc florets; and
4. Plants of the new *Gerbera* cultivar 'UFGE 7031' and the male parent 'UFGE 5015' differ in powdery mildew resistance as the plants of the male parent are highly susceptible to powdery mildew.

The new *Gerbera* cultivar 'UFGE 7031' can be compared to *Gerbera hybrida* 'UFGE 4141', disclosed in U.S. Plant Pat. No. 23,346. Plants of the new *Gerbera* cultivar 'UFGE 7031' differ from plants of 'UFGE 4141' in the following characteristics:

1. Plants of the new *Gerbera* cultivar 'UFGE 7031' and 'UFGE 4141' differ in inflorescence form as plants of 'UFGE 4141' have semi-double inflorescences;
2. Ray florets of the new *Gerbera* cultivar 'UFGE 7031' are less red than the ray florets of 'UFGE 4141' (RHS 33B);
3. Plants of the new *Gerbera* cultivar 'UFGE 7031' and 'UFGE 4141' differ in disc floret color as plants of 'UFGE 4141' have a yellow-green disc before opening of disc florets; and
4. Plants of the new *Gerbera* cultivar 'UFGE 7031' have shorter peduncles as the peduncles of 'UFGE 4141' are approximately 52 cm.

The new *Gerbera* cultivar 'UFGE 7031' can be compared to *Gerbera hybrida* 'UFGE 7034', disclosed in U.S. Plant Pat. No. 23,433. Plants of the new *Gerbera* cultivar 'UFGE 7031' differ from plants of 'UFGE 7034' in the following characteristics:

1. Plants of the new *Gerbera* cultivar 'UFGE 7031' and 'UFGE 7034' differ in inflorescence form as plants of 'UFGE 7034' have double inflorescences;
2. Plants of the new *Gerbera* cultivar 'UFGE 7031' and 'UFGE 7034' differ in disc floret color as plants of 'UFGE 7034' have a yellow-green (RHS 151D) disc before opening of the disc florets; and
3. Plants of the new *Gerbera* cultivar 'UFGE 7031' have higher levels of powdery mildew resistance than plants of 'UFGE 7034'.

DESCRIPTION OF THE FIGURES

This new *Gerbera* cultivar 'UFGE 7031' is illustrated by the accompanying photographs (FIGS. 1-3) which show the plant's form, inflorescences, and foliage. The colors shown are as true as can be reasonably obtained by conventional photographic procedures. The photographs are of a plant approximately five months old which was produced from one tissue culture liner and was potted in a 2.7-L container. Colors in the photograph may differ slightly from the color values cited in the detailed botanical description, which accurately describe the colors of the new *Gerbera* cultivar.

DETAILED BOTANICAL DESCRIPTION

Figure 1:
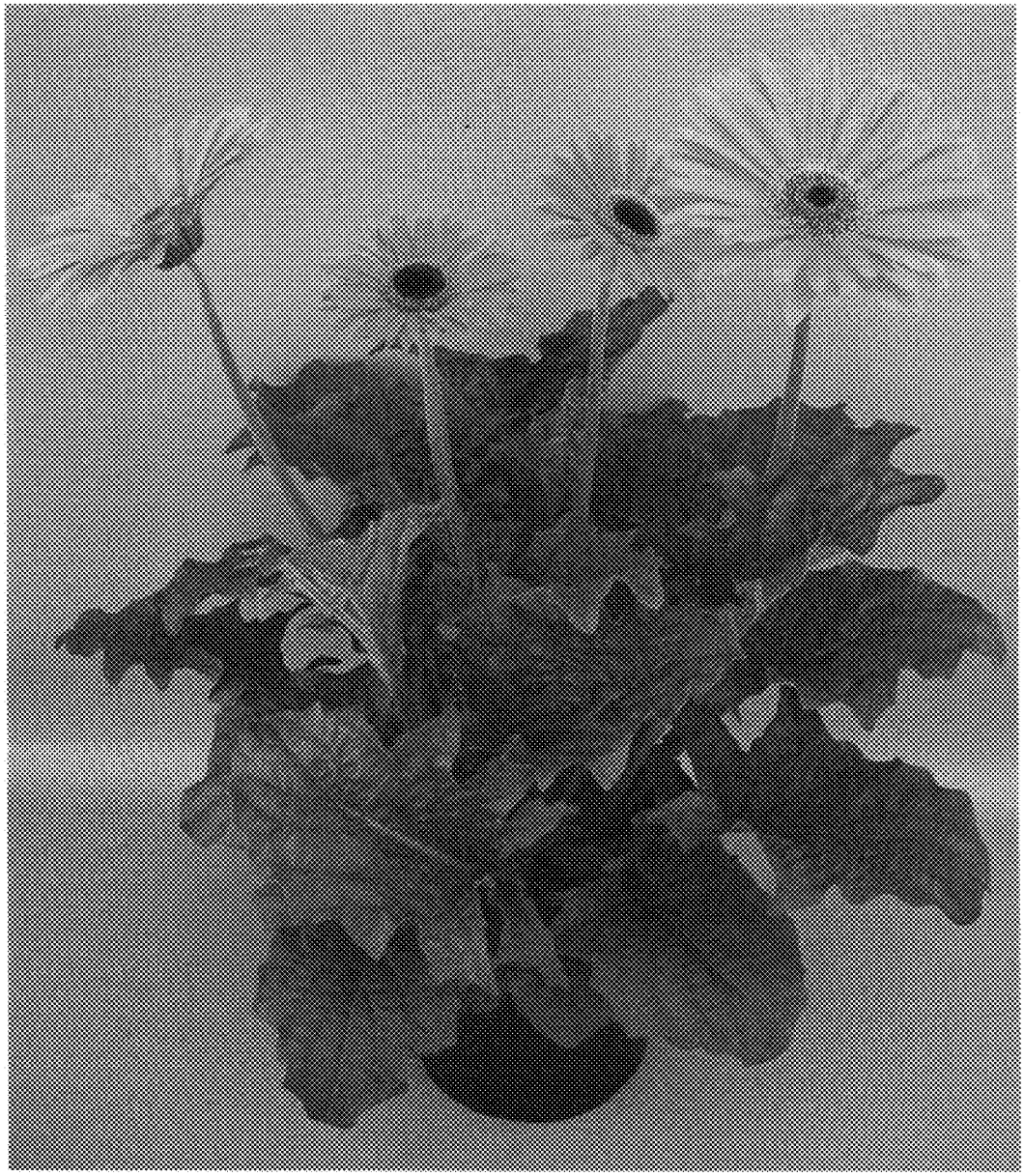
FIG. 1 shows a photograph of the overall plant habit including inflorescences and foliage of a typical plant of the new *Gerbera* cultivar 'UFGE 7031'. The photograph of FIG. 1 is taken from a side perspective view.
Figure 2:
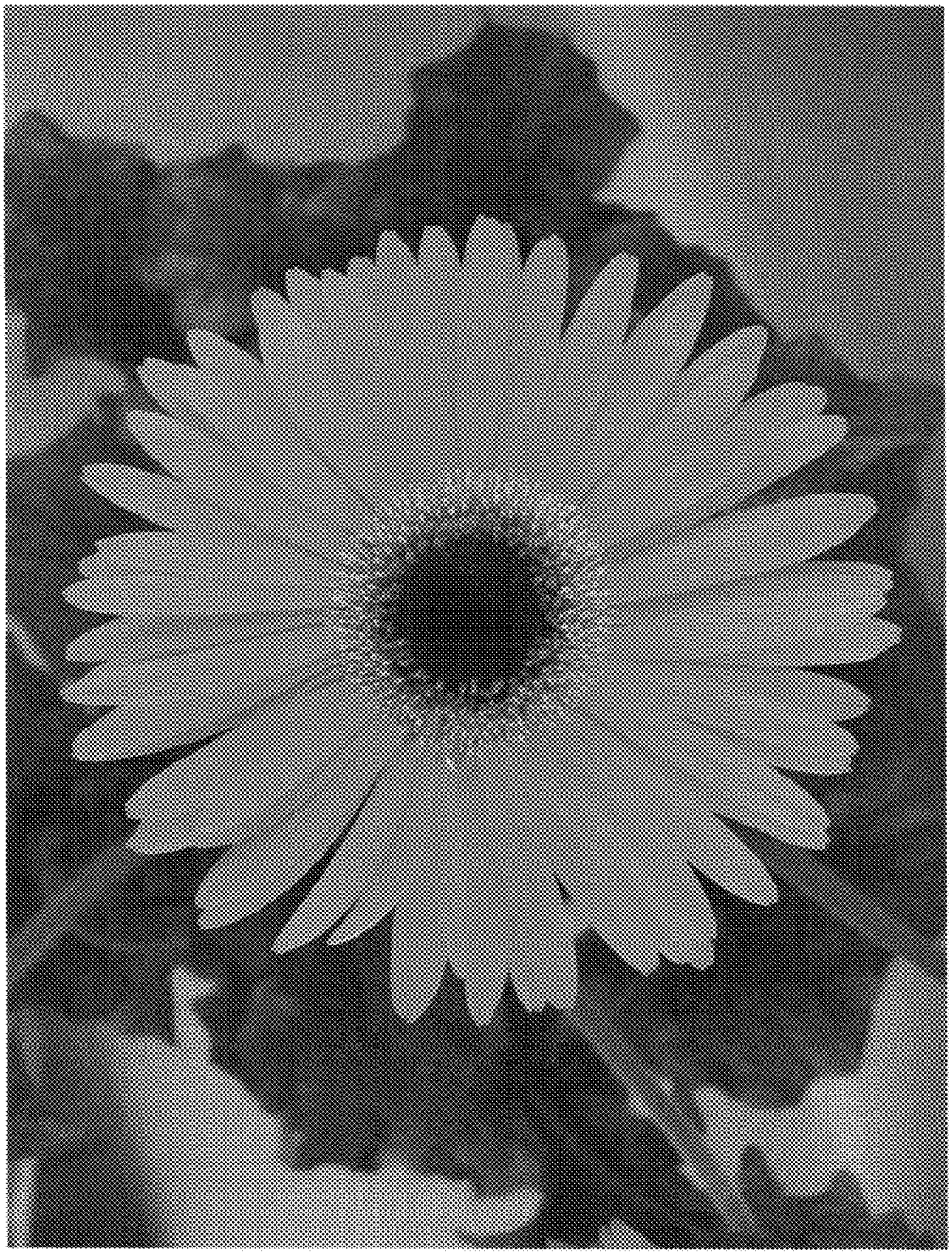
FIG. 2 shows a photograph illustrating a close-up view of an inflorescence of a typical plant of the new *Gerbera* cultivar 'UFGE 7031'.
Figure 3:
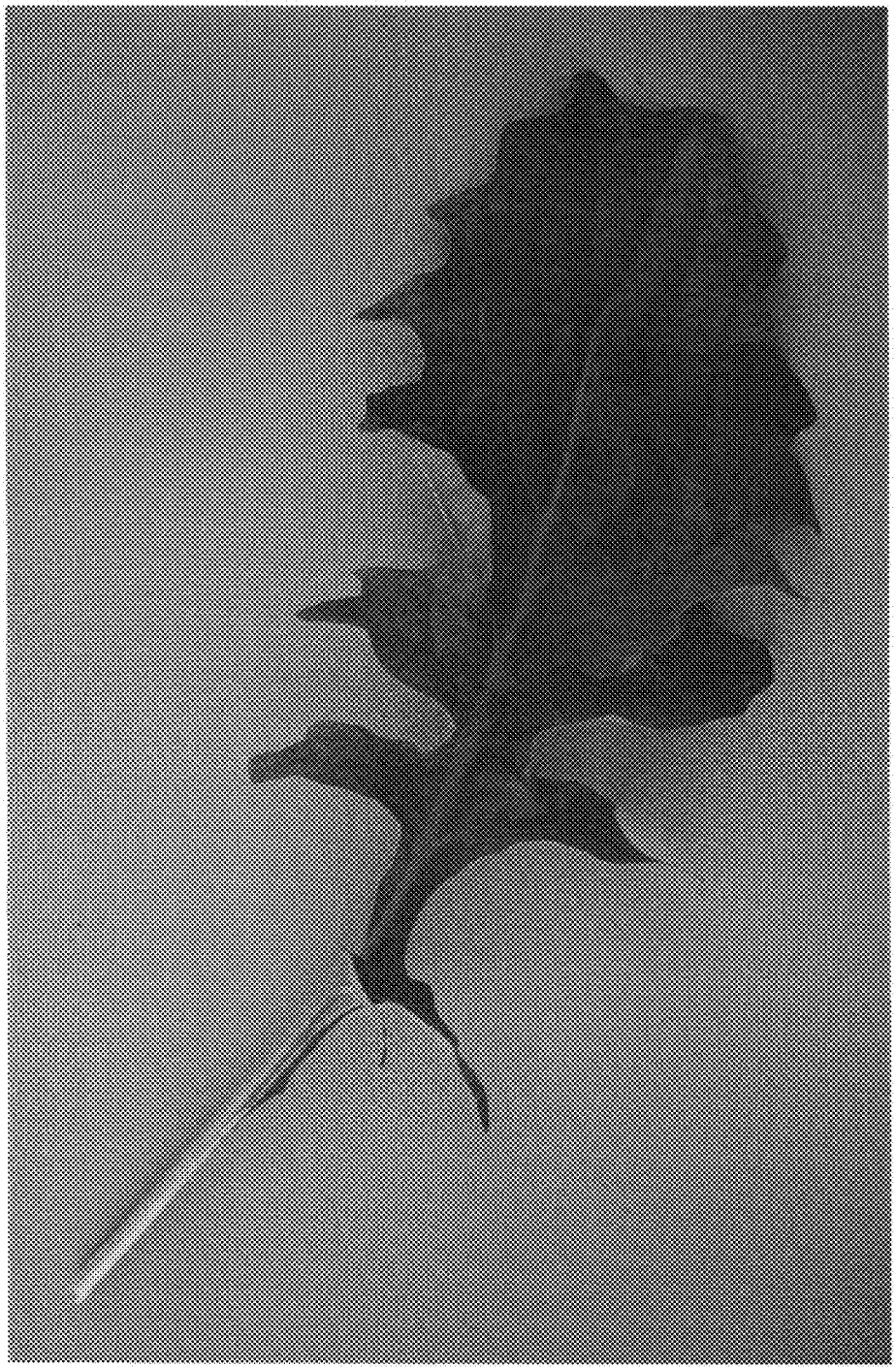
FIG. 3 shows a photograph illustrating a close-up of a leaf of a typical plant of the new *Gerbera* cultivar 'UFGE 7031'.

The following detailed description sets forth the distinctive characteristics of the new *Gerbera* cultivar 'UFGE 7031'. The present botanical description is based on plants of the new *Gerbera* cultivar 'UFGE 7031', and the plants were approximately seven months old when the data was taken. The colors (except those in common terms) are described from R.H.S. Colour Chart published by The Royal Horticultural Society in London (1986 ed.), in association with the Flower Council of Holland.

BOTANICAL DESCRIPTION

Botanical classification:

*Family*.—Asteraceae.

*Botanical name*.—*Gerbera hybrida* 'UFGE 7031'.

*Common name*.—*Gerbera* (*Gerbera*).

Parentage:

*Female, or seed, parent*.—'UFGE 5004' (unpatented, proprietary breeding line).

*Male, or pollen, parent*.—'UFGE 5015' (unpatented, proprietary breeding line).

Plant description:

*General appearance*.—Herbaceous perennial, typically grown as container or garden plants; upright and mounding growth habit, roughly globular in shape; leaves arranged in basal rosettes and outwardly arching; dense and bushy habit; inflorescences held above the foliar plane on erect and strong basal peduncles (or scapes); moderately vigorous.

*Plant height, soil level to top of foliar plane*.—Approx. 27 cm.

*Plant height, soil level to top of inflorescence*.—About 45 cm.

*Plant width*.—Approx. 60 cm.

Foliage description:

*Leaf arrangement*.—Basal rosette, alternate, simple.

*Leaf blade*.—Length: Approx. 24 cm. Width: Approx. 16 cm. Shape: Oblong. Apex: Moderately acute to obtuse. Base: Truncate. Margin: Irregular crenate, sinuses divergent, undulate. Texture, upper surface: Sparsely pubescent. Texture, lower surface: Moderately pubescent. Venation pattern: Pinnate. Depth of incisions in leaf: Basal part: Deep. Central part: Medium. Distal part: Shallow. Color, Upper side: Yellow-green (RHS 147A) but darker. Color, Bottom side: Yellow-green (RHS 147B). Glossiness on upper side: Medium.

*Petiole*.—Petiole length: Approx. 9 cm. Diameter: About 4 mm. Texture, upper and lower surfaces: Moderately pubescent. Color, upper and lower surfaces: Close to yellow-green (RHS 144A). Color, proximal end: Close to yellow-green (RHS 144B to 144D). Petiole anthocyanin coloration at the proximal end: Strong to weak or absent; close red-purple (RHS 60B and 60C) if coloration is strong.

Inflorescence:

*Appearance*.—Single type inflorescence form; solitary inflorescences borne on upright and strong scapes above the foliar plane; ray and disc florets arranged acropetally on a capitulum.

*Color* (*general tonality from a distance of* 3 *meters*).—Orange-red (RHS 30C).

*Shape*.—Moderately incurving funnel-shaped.

*Fragrance*.—None detected.

*Flowering season*.—Plants begin flowering about six weeks after planting tissue culture liners and flower year-round in outdoor gardens in Wimauma, Fla., until plants are killed by frosts or freezes; plants flower year-round under greenhouse conditions in Wimauma, Fla.

*Inflorescence longevity*.—Inflorescences last about two weeks on the plant in Wimauma, Fla.; inflorescences not persistent.

*Quantity of inflorescences*.—Free flowering habit, with up to 20 open and developing inflorescences per plant at a time.

*Inflorescence bud*.—Height: About 1 cm. Diameter: About 2 cm. Shape: Oblate. Color (opening buds): Close to greyed-purple (RHS 187A) but darker.

*Inflorescence size*.—Diameter: About 11 cm. Depth (height): About 1.9 cm. Diameter of disc: About 2.5 cm. Receptacle height: About 2 mm. Receptacle diameter: About 1.8 cm. Receptacle color: Close to green-white (RHS 157A).

*Phyllaries*.—Number of phyllaries per inflorescence: About 57 arranged in about three whorls. Length: About 1.2 cm. Width: About 2 mm. Shape: Subulate. Apex: Narrowly acute. Base: Truncate. Margin: Entire. Texture, upper surface: Smooth, glabrous. Texture, lower surface: Moderately tomentose. Color, inner surface: Close to green (RHS 144A). Color, outer surface: Close to green (RHS 137C). Color, towards the base: Close to green (RHS 137B).

*Inner ray florets* (*trans florets*).—Number per inflorescence: About 185 arranged in about four whorls. Length: About 10 mm. Width: About 2 mm. Shape: Tubular, fused. Apex: Emarginate to obtuse. Base: Truncate. Margin: Entire. Texture, upper surface: Smooth, glabrous, slightly velvety, longitudinally ridged. Texture, lower surface: Smooth, glabrous, slightly velvety, longitudinally ridged. Color, upper surface: Close to red (RHS 45B). Color, lower surface: Close to red (RHS 45D).

*Outer ray floret*.—Number: About 58 arranged in three whorls. Cross section: Straight to slightly convex. Length: Medium, approx. 5.3 cm. Width: Medium, approx. 8 mm. Shape: Narrow elliptic. Apex: Emarginate to obtuse. Base: Truncate. Margin: Entire. Depth of incision: None to very shallow. Texture, upper surface: Smooth, glabrous, slightly velvety, longitudinally ridged. Texture, lower surface: Smooth, glabrous, slightly velvety, longitudinally ridged. Color (topside): Close to orange-red (RHS 30C and 30D); proximal end: close to yellow (RHS 12B). Color (bottom side): Variable with stage of inflorescence development; Close to yellow-orange (RHS 26C) with streaks of orange-red (RHS 32C) and proximal end of yellow (RHS 12B), or close to yellow (RHS 3C) with streaks of orange-red (RHS 31B) and proximal end of yellow (RHS 12B).

*Disc florets*.—Number: About 330. Length: About 1.2 cm. Width: About 3 mm. Shape: Tubular, fused. Apex: Narrowly obtuse. Base: Fused. Margin: Entire. Texture, upper and lower surfaces: Smooth, glabrous. Color, fully opened upper surface: Close to red (RHS 45B). Color, fully opened lower surface: Close to red (RHS 45D).

*Reproductive organs*.—Androecium: On most disc florets; quantity: one. Gynoecium: On ray and disc florets; quantity per floret: one. Filament length: About 4 mm. Filament color: Close to yellow-white (158A). Anther shape: Linear. Anther length: About 3 mm. Anther width: About 1 mm. Anther color: Close to yellow (RHS 13C). Pollen, amount: Fair. Pollen color: Close to yellow (RHS 8B). Pistil per floret: One. Pistil length: About 1.6 cm. Stigma shape: Cleft. Stigma color: Close to yellow (RHS 8C). Style length: About 1.2 cm. Style color: Close to yellow (RHS 8B). Ovary color: Close to white (RHS 155A).

*Pappus*.—Quantity of hairs per floret: About 93. Length: About 7 mm. Diameter: Less than 1 mm. Texture: Soft. Main color: Close to yellow-white (RHS 158D).

*Peduncle*.—Length: Medium, approx. 41 cm. Tendency to fasciation: Absent. Diameter: Medium, approx. 5.5 mm. Strength: Strong. Texture: Moderately tomentose. Color: Close to yellow-green (RHS 144A). Anthocyanin coloration, at base and top: Absent.

Resistance to diseases: Plants of the new *Gerbera* cultivar 'UFGE 7031' were observed in five experiments in which they were compared with plants of commercial *Gerbera* cultivars, 'Bimini' (unpatented), 'Pensacola' (unpatented), 'FUNTASTIC™ Canary' ('UFGE 7032'), and/or 'FUNTASTIC™ Fire Orange' ('UFGE 4141'), for the severity of powdery mildew, *Podosphaera* (syn. *Sphaerotheca*) *fusca* (Fr.) S. Blumer. Plants of the new *Gerbera* cultivar 'UFGE 7031' consistently showed a high level of resistance to powdery mildew. The five experiments were conducted in Wimauma, Fla.: Experiment 1 was conducted from winter 2008 to spring 2009, Experiments 2 and 3 were conducted from summer to fall 2009, and Experiments 4 and 5 were conducted from spring to summer 2012. In all experiments, tissue culture liners of the new *Gerbera*, 'Bimini', 'Pensacola', 'FUNTASTIC™ Canary', and/or 'FUNTASTIC™ Fire Orange' were transplanted into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. In Experiments 1, 3 and 4, all plants were grown in a screen house in Wimauma, Fla., without temperature or photoperiod control but with approximately 45% light exclusion. In Experiments 2 and 5, plants were grown in a greenhouse in Wimauma, Fla. The greenhouse had approximately 30% light exclusion and temperature inside the greenhouse was between 21° C. (night) to 35° C. (day). Fungicides were not applied throughout the experiments to subject the plants to natural powdery mildew disease pressures. A randomized complete block design was used in these experiments, with five (Experiment 1), five (Experiment 2), six (Experiment 3), four (Experiment 4), or six (Experiment 5) replications. The experimental unit was a single containerized plant. Severity of powdery mildew on plants was assessed using a scale of 1 to 10 as described by Hausbeck et al. (2002) in March 2009 (Experiment 1), June 2009 (Experiment 2), October 2009 (Experiment 3), and August 2012 (Experiments 4 and 5). Plants of the new *Gerbera* cultivar received the lowest powdery mildew severity ratings in all experiments, and its rating was below 3.0 in four experiments. These results indicate a high level of powdery mildew resistance in the new *Gerbera* cultivar. No other disease resistance characterizations have been made. Table 1. Powdery mildew severity ratings of the new *Gerbera* cultivar 'UFGE 7031' and commercial *Gerbera* cultivars, 'Bimini', 'Pensacola', 'FUNTASTIC™ Canary', and/or 'FUNTASTIC™ Fire Orange', grown under natural powdery mildew pressure in five experiments in Wimauma, Fla.: Experiment 1 (winter 2008 through spring 2009), Experiments 2 and 3 (summer 2009 through fall 2009), and Experiments 4 and 5 (spring 2012 through summer 2012).

| | Experiments | | | | |
|---|---|---|---|---|---|
| | 1 | 2 | 3 | 4 | 5 |
| Varieties | Powdery mildew severity ratings[z] | | | | |
| New Gerbera | 3.6 | 2.7 | 1.7 | 1.4 | 1.0 |
| 'Bimini' | 7.5 | 6.7 | | | |
| 'Pensacola' | 8.6 | 8.7 | | | |
| 'FUNTASTIC ™ Canary' | 7.4 | 5.7 | 4.2 | 3.3 | 2.8 |
| 'FUNTASTIC ™ Fire Orange' | 6.8 | 4.0 | 3.7 | | |

[z]Powdery mildew severity was rated on a scale of 1 to 10 as described by Hausbeck et al. (2002): 1 = no disease, 2 = trace to 10%, 3 = 10% to 20%, 4 = 20 to 30%, 5 = 30% to 40%, 6 = 40% to 50%, 7 = 50% to 60%, 8 = 60% to 70%, 9 =70% to 80%, and 10 = 80% to 100% of leaf surface covered with powdery mildew.

Heat tolerance: Plants of the new *Gerbera* cultivar 'UFGE 7031' grow well and produce inflorescences freely in summer in Florida when ambient temperatures are 35° C. or higher.

LITERATURE CITED

Hausbeck, M. K., W. R. Quackenbush, and S. D. Linderman. 2002. Evaluation of cultivars of African daisy for resistance to powdery mildew, 2002. B&C Tests 18:O0004.

What is claimed is:

1. A new and distinct cultivar of *Gerbera* plant named 'UFGE 7031', as illustrated and described herein.

* * * * *